US010836892B2

(12) United States Patent
Jakuczek et al.

(10) Patent No.: US 10,836,892 B2
(45) Date of Patent: Nov. 17, 2020

(54) PART CONSISTING OF A MATERIAL AND A METHOD OF MANUFACTURING SUCH PART AND A METHOD OF RADIATION STERILIZATION OF SUCH PART

(71) Applicant: Datwyler Pharma Packaging International NV, Alken (BE)

(72) Inventors: Leszek Jakuczek, Hasselt (BE); Luc Vanderheyden, Hasselt (BE); Agna Francis, Gingelom (BE)

(73) Assignee: Datwyler Pharma Packaging International NV, Alken (BE)

( * ) Notice: Subject to any disclaimer, the term of this patent is extended or adjusted under 35 U.S.C. 154(b) by 611 days.

(21) Appl. No.: 14/901,364

(22) PCT Filed: Jul. 12, 2013

(86) PCT No.: PCT/EP2013/064827
§ 371 (c)(1),
(2) Date: Dec. 28, 2015

(87) PCT Pub. No.: WO2015/003752
PCT Pub. Date: Jan. 15, 2015

(65) Prior Publication Data
US 2016/0137825 A1   May 19, 2016

(51) Int. Cl.
*C08L 23/22* (2006.01)
*A61L 2/08* (2006.01)
(52) U.S. Cl.
CPC ........... *C08L 23/22* (2013.01); *A61L 2/081* (2013.01); *A61L 2/082* (2013.01); *A61L 2/087* (2013.01); *C08L 2203/02* (2013.01); *C08L 2205/02* (2013.01); *C08L 2205/03* (2013.01); *C08L 2205/035* (2013.01)
(58) Field of Classification Search
CPC .......... C08L 23/22; A61L 2/081; A61L 2/082; A61L 2/087
See application file for complete search history.

(56) References Cited

U.S. PATENT DOCUMENTS

| | | | | |
|---|---|---|---|---|
| 4,018,659 A | | 4/1977 | Marek et al. | |
| 5,597,867 A | * | 1/1997 | Tsujimoto | C08K 5/54 525/74 |
| 5,621,045 A | * | 4/1997 | Patel | C08L 7/00 525/194 |
| 6,069,202 A | * | 5/2000 | Venkataswamy | C08L 77/00 525/133 |
| 6,084,031 A | * | 7/2000 | Medsker | C08F 8/42 525/192 |
| 6,143,805 A | | 11/2000 | Hickey et al. | |
| 6,248,800 B1 | | 6/2001 | Greff et al. | |
| 6,743,858 B2 | | 6/2004 | Hickey et al. | |
| 7,060,753 B2 | * | 6/2006 | Jacob | C08K 5/0008 525/191 |
| 7,282,535 B2 | * | 10/2007 | Kakeda | C08F 293/005 525/88 |
| 7,445,846 B2 | * | 11/2008 | Jacob | B32B 25/04 428/421 |
| 8,177,665 B2 | * | 5/2012 | Loper | A63B 37/0003 473/376 |
| 2003/0119988 A1 | * | 6/2003 | Johnson | C08L 23/16 525/191 |
| 2009/0076214 A1 | * | 3/2009 | Kiss | C08F 10/00 524/570 |
| 2010/0197862 A1 | | 8/2010 | Kawauchi et al. | |
| 2010/0249296 A1 | | 9/2010 | Kimura et al. | |
| 2011/0071635 A1 | | 3/2011 | Zhang et al. | |

FOREIGN PATENT DOCUMENTS

| | | |
|---|---|---|
| EP | 1 006 151 A1 | 6/2000 |
| EP | 2 006 328 A1 | 12/2008 |
| EP | 2 172 515 A1 | 4/2010 |
| WO | 2007/065152 A2 | 6/2007 |
| WO | 2010/135244 A2 | 11/2010 |
| WO | 2012/166779 A2 | 12/2012 |

OTHER PUBLICATIONS

International Search Report of PCT/EP2013/064827, dated Aug. 26, 2013.
Written Opinion of the International Searching Authority in PCT/EP2013/064827, dated Aug. 26, 2013.
ASTM D1238, Standard Test Method for Melt Flow Rates of Thermoplastics by Extrusion Plastometer, Mar. 2010, pp. 1-15.
Din En ISO 1133-1, Plastics—Determination of the melt mass-flow rate (MFR) and melt volume-flow rate (MVR) of thermoplastics—Part 1: Standard method (ISO 1133-1:2011), Mar. 2012, pp. 1-29.
ISO 11357-1, Plastics—Differential scanning calorimetry (DSC)—Part 1: General principles, Second edition Oct. 15, 2009, 40 pages.
ISO 11357-2, Plastics—Differential scanning calorimetry (DSC)—Part 2: Determination of glass transition temperature and glass transition step height, Second edition May 1, 2013, 12 pages.
ISO 7619-1, Rubber, vulcanized or thermoplastic—Determination of indentation hardness—Part 1: Durometer method (Shore hardness), Second edition Oct. 1, 2010, 20 pages.

(Continued)

*Primary Examiner* — Regina M Yoo
(74) *Attorney, Agent, or Firm* — Collard & Roe, P.C.

(57) ABSTRACT

The material of a part includes a composition obtained by blending an isobutylene-based, pre-crosslinked polymer as component (A), at least one poly olefin or a non-crosslinked rubber or a TPV as component (B), at least one polymer having a Tg of 90° C. or higher as component (C) and—preferably—at least one component (D) selected from the group of: substituted vinyl polymers, stryrenic block copolymers, inorganic functionalized and non-functionalized fillers, carbon black, halogen scavengers, preferably the inorganic halogen scavengers, acid acceptors, stabilizers, preferably the polymeric stabilizers, and processing aids.

11 Claims, No Drawings

(56) References Cited

OTHER PUBLICATIONS

ISO 815-1, Rubber, vulcanized or thermoplastic—Determination of compression set—Part 1: At ambient or elevated temperatures, Second edition Sep. 1, 2014, 18 pages.
J.E. Mark, Physical Properties of Polymers Handbook, Second Edition, 2007, pp. 217-223 (15 pages).
DIN EN ISO 1133-1, Plastics—Determination of the melt mass-flow rate (MFC) and melt volume-flow rate (MVR) of thermoplastics—Part 1: Standard method (ISO 1133-1:2011), Mar. 2012, pp. 1-29.
DIN 53 765, Mar. 1994, pp. 1-12.

* cited by examiner

US 10,836,892 B2

PART CONSISTING OF A MATERIAL AND A METHOD OF MANUFACTURING SUCH PART AND A METHOD OF RADIATION STERILIZATION OF SUCH PART

CROSS REFERENCE TO RELATED APPLICATIONS

This application is the National Stage of PCT/EP2013/064827 filed on Jul. 12, 2013, the disclosure of which is incorporated by reference. The international application under PCT article 21(2) was published in English.

FIELD OF THE INVENTION

The present invention relates to parts in general consisting of materials more specifically outlined below. Especially, such parts can be pharmaceutical seals, particularly in form of vial stoppers and syringe gaskets. Additionally, the invention addresses a method for sterilization of such parts, which again can be specifically pharmaceutical seals, in particular closures produced from TPV and/or TPE materials comprising isobutylene monomer units. More specifically the invention relates also to a method for sterilization of such parts, which also in this respect can be particularly pharmaceutical seals, especially in form of vial closures and syringe gaskets as further described.

BACKGROUND OF THE INVENTION

The parts and the methods disclosed herein are independent of a specific use, however, the possible use is explained by way of example in the following sections with the focus on pharmaceutical parts, especially pharmaceutical seals.

Elastomeric components or parts, especially such components or parts designed for applications, in which the pharmacological compatibility of the elastomeric components is an issue, are known in many different forms, especially as closure means for pharmacological containers, such as serum stoppers, infusion stoppers, sealing elements for spraying devices (e.g. O-rings), diagnostic closure systems, injection pen systems or syringe gaskets. The requirements, hence specifications, for elastomeric components or parts in said applications are strict and highly demanding. Those specifications for example require stoppers from elastomeric materials that release no substances, which could negatively affect the therapeutic action of the injected preparation.

The specifications for rubber parts, i.e. parts which are made from an elastomeric material, e.g. in medical areas, which further e.g. come into contact with drug solutions, suspensions or powders during their preparation, storage and use, are generally established by pharmacopoeia standards.

The compliance with aforementioned standards is not necessary for the parts disclosed here. However, in a more specific aspect, it is preferred, that the parts do comply with those standards. The compliance with such standard, but also other aspects can be facilitated by the proper selection of the suitable components. However, in case of e.g. both thermoset rubber and thermoplastic elastomers/vulcanizates, or in general, certain compromises about the compound/material must usually be accepted to provide a good balance of physical, chemical and functional properties of the final product.

For many advanced applications, particularly when the encapsulated drug stays in a long-term contact with the elastomeric part, it is vitally important to maintain the proper functionality of biologically active drug components. Therefore, the substances that may be extracted or leach from the material (further described as "extractables and leachables") and come into interaction with a drug or its components have become over last few years one of the main subjects of intensive studies. The progress in the field of analytical techniques has resulted in an increased concern about the by-products of polymerization and crosslinking processes, oligomers and metal cations present even in the cleanest thermoset rubber formulations and which can impair the efficiency of certain medicines.

Irrespective of the above-mentioned extractables and leachables issue the thermoset rubber systems show some general deficiencies. The mixing, molding and finishing process in the rubber industry are in general quite labour- and time-consuming, generate significant amount of waste and comprise a number of operations (process complexity). Due to the latter feature the risk of microbiological contamination increases with the number of operations, so very robust washing and sterilization procedures are required to assure sufficient product cleanliness. The freedom of product design and automation of the process are also affected by that. Finally, overmolding techniques remain largely inapplicable in case of thermoset rubbers.

With respect to that, thermoplastic rubber (based on either thermoplastic vulcanizates-TPV's or thermoplastic elastomers-TPE's) formulations has started to constitute an interesting option to avoid or reduce the extractables and leachables typical for thermoset rubbers for pharmaceutical closure systems.

The polyisobutylene-based thermoplastic vulcanizates have been developed in the last few years. Such materials combine very good physical performance such as reduced compression set values, good elasticity and gas barrier properties with good chemical cleanliness.

Basically two major approaches towards the butyl-based, clean TPV/TPE materials have been discussed in the technical literature with the differences observably mainly for the dynamic crosslinking mechanism. One of them is based on the peroxides, the other (noticeably more popular) on the hydrosilylation process. The patent EP 1006151 by Advanced Elastomer Systems teaches about the TPV system based on the acrylic-modified halogenated paramethylstyrene-isobutylene rubber produced by crosslinking the rubber component (further modified by addition of some polyolefin and process oils) with the platinum-based catalyst. The catalysts for such processes can also be based on other rare metals like palladium and rhodium, but the platinum systems are the most frequently mentioned. A similar approach of hydrosilylation is further presented in patents filed by Kaneka Corporation and Daikyo Seiko Ltd. from Japan, when the allyl-functionalized isobutylene-based polymer with terminal groups capable of undergoing hydrosillylation reaction is crosslinked in presence of a styrenic block copolymer, a polyolefin component, platinum-containing catalyst, polysiloxane-based crosslinking agent and some further additives. The corresponding documents as the US patent nr 2010/0249296 by Kimura K. or the US 2010197862 by Kawauchi Y., Kimura K. are hereby incorporated by reference. The aforementioned process has led to the commercialization of the SIBSTAR TPV family by the Kaneka Corporation.

Such butyl-based TPVs were further used to provide the TPE-compounds showing acceptable cleanliness and compression set. The patent documents issued by the PolyOne Corporation teach about compounds for use in food-related applications (the WO2010135244) or compounds that are characterized by low compression set and barrier properties (WO2012166779). The latter document discloses a thermoplastic elastomer compound, that shows an interesting combination of compression set and barrier properties. However, on the other hand the proposed formulation contains substantial amount of oils and other processing aids. Although such a combination may be of some advantage concerning processability, it is simultaneously going to cause problems from the perspective of a long term use in pharmaceutical packaging.

Naturally, the final performance of the compound used for pharmaceutical closures turns out to depend not only on the selection of chemical components, but is also strongly affected by its internal morphology, particularly defined by the state of dispersion achieved for certain additives.

All the elastomeric products for use in pharmaceutical packaging need to be sterilized prior to use. Nowadays, the most popular sterilization technologies include thermal (with steam), radiation (UV, gamma, beta (e-beam) or X-rays) and chemical sterilization (ethylene oxide—ETO, hydrogen peroxide—HP). Over the last few years there is a growing interest in non-thermal sterilization techniques, especially in the field of gamma sterilization. For the TPE and TPV materials that are either uncured or characterized by only low crosslink density, the radiation treatment has several clear advantages over thermal sterilization, which takes place under temperatures exceeding thermal glass transition points of most of the common plastics, e.g. there is less risk of product deformation or displacement, when the elastomeric part is integrated into the total packaging system, e.g. a capped vial or a syringe. The commonly applied methods of radiation sterilization include exposure of the material (in form of pharmaceutical seals) to gamma or X-ray radiation, electron beam irradiation, UV and microwave irradiation provided at the doses sufficient to reach desired level of sterility. Sterilization methods utilizing beta (electron beam) or gamma radiation, as described in U.S. Pat. Nos. 6,743,858; 6,248,800; and 6,143,805, are preferred with respect to the parts for pharmaceutical packaging.

The modern chemical sterilization constitutes another option. Such a sterilization can be carried out preferably by using hydrogen peroxide ($H_2O_2$; further denoted HP), even more preferably by using the vaporized hydrogen peroxide (VHP). The hydrogen peroxide solutions have been used as chemical sterilants for many years. However, the VHP was not developed for the sterilization of medical equipment until the mid-1980s. One method for delivering VHP to the reaction site uses a deep vacuum to pull liquid HP (30% concentration) from a disposable cartridge through a heated vaporizer and then, following vaporization, into the sterilization chamber. A second approach to VHP delivery is the flow-through approach, in which the VHP is carried into the sterilization chamber by a carrier gas such as air using either a slight negative pressure (vacuum) or slight positive pressure.

Concerning the radiation sterilization, one must stress that the specificity of high energy radiation with its capability to start undesired reactions in the material requires a modified approach in formulating the compounds for pharmaceutical seals. It is commonly known, that the sterilization of parts by beta or gamma radiation under standard conditions, particularly those parts consisting of homo- co- and terpolymers of isobutylene leads to observable degradation of the polymer matrix, accompanied e.g. by the formation of chemically active functional groups (acidic, carbonylic, etc.). This limits the usefulness of such compounds in many applications despite the advantages inherent in such products. Particularly, it limits their usefulness in compositions and blends for the pharmaceutical industry when the intention was to sterilize or cure such material compositions or blends by irradiation without sacrificing their high cleanliness.

It is equally generally well known, that in consequence of the radiation treatment of polymers free radicals are formed that are responsible for consequent cross-linking and chain scission reactions ongoing in the bulk material. The ultimate properties of the irradiated product will depend on the sterilization conditions (defined by the dose and environment) that determine the outcome of aforementioned reactions.

In case of polyisobutylene and butyl rubber the irradiation results generally in material degradation due to predominant chain scission processes—unless the polymers are stabilized by either chemical modification (halogenation) or by the presence of some other additives (e.g. special fillers and irradiation-resistant polymers). The usual consequence is the deterioration of mechanical, chemical and functional properties of the final products (seals) manifested e.g. by softening, increased stickiness, different sealing performance, different stress relaxation behavior, increased creep compliance and significant worsening of chemical cleanliness of the material. That becomes particularly noticeable in case of the butyl-based TPV/TPE combinations.

From the introduction it is therefore clear that there exists a need to provide elastomeric components of the aforementioned kind and parts thereof, which show the combination of expected physical, barrier and functional properties, an improved chemical inertness, provides low levels of extractables and leachables, good resistance towards solvents and solutions within a wide pH range, reduced stickiness, long term stability (shelf-life) along with reasonable moldability/processability properties.

Starting from this, it is an object of the reported invention, to provide a material, parts made thereof and/or a method to produce parts from such material, which contains no or only very small amount of plasticizers and will be in terms of pharmaceutical use a clean material, nevertheless soft.

Furthermore, there also exists a need for pharmaceutical seals/closures withstanding sterilization by irradiation and still maintaining high performance standards. As a result of an extensive research program, the composition of advanced elastomer compounds for e.g. pharmaceutical seals (e.g. stoppers, syringe gaskets, etc.) and a proper process design were identified as key factors ensuring the maximal final integrity of drug delivery systems.

With respect to the latter, the impact of optimized sterilization procedures alleviating the irradiation-related problems as observed for the pharmaceutical closures produced from butyl-based TPV/TPE materials has not become—to our best knowledge—subject of detailed studies until now. The present invention calls for an improved sterilization method, which allows current TPV/TPE based closures to better withstand sterilization by irradiation and lower the negative impact of such treatment on material properties.

SUMMARY OF THE INVENTION

The present invention concerns further a part consisting of a material comprising the following, especially a radiation sterilisable pharmaceutical seal comprising:
(a) a composition obtained by blending an isobutylene-based, preferably pre-crosslinked polymer as component (A) with
(b) at least one polyolefin or a non-crosslinked rubber or a TPV as component (B)

(c) at least one polymer having a Tg of 90° C. or higher as component (C) and (d)—preferably—at least one component (D) selected from the group of: substituted vinyl polymers, styrenic block copolymers, inorganic functionalized and non-functionalized fillers, carbon black, halogen scavengers, especially the inorganic halogen scavengers, acid acceptors, stabilizers, especially the polymeric stabilizers and processing aids.

Component (A) preferably is a cross-linked isobutylene-based TPV material having a hardness value ranging between 15-85, more preferably between at least 25 and 75 and even more preferably between 40 and 65° ShA.

Component (B) preferably is chosen from the group consisting of ethylene, propylene, 1-butene, isoprene or isobutylene homopolymers, cyclic olefin copolymers, co- or terpolymers of ethylene, propylene, isoprene, isobutylene and other dienes different from isoprene or a combination of them used in a non-treated or chemically modified form (e.g. halogenated), whereby the latter co- and terpolymers are preferably in a non-crosslinked state or used as a preformulated TPV and whereby the component B, preferably has a melt flow index (MFI) value ranging between 0.1 and 75, preferably between 1 and 65 and more preferably between 1 and 50 g/10 min and whereby e.g. an ethylene-cyclic olefin copolymer (COC) component is characterized by a Tg value ranging between 75 and 200° C., more preferably between 110 and 180° C.

Component (C) is preferably selected from the group comprising: polyimide, polyether-imide, polyamide-imides, polyetherketone, aliphatic and aromatic polyamides, aliphatic and aromatic polyesters, polyphenylene sulfide or polyphenylene ether.

Said component C comprises at least one polymer exhibiting a Tg value of at least 90° C.

To have further incorporated at least one of the components mentioned under (D) is preferred, but not necessary in a first approach. According to a preferred embodiment, the composition comprises as component D syndiotactic polystyrene.

Preferably, neither the material nor the pharmaceutical part constituting the object of the reported invention, irrespectively of the method of their production, contain any low molecular weight processing oil or only a minor amount of it. The same applies to the polymeric components used to facilitate the introduction of typical processing oils—e.g. SEEPS block copolymers.

Although the inventors do not wish to be bound by any theoretical reasoning, it is believed that the blend composition of this invention is characterized by a reduction of the degradation induced by radiation sterilization. This is the result of a more efficient radical scavenging by the carefully selected ingredients as well as by the specific morphology of the blend.

Overall, the compositions of the present invention overcome the deficiencies described above, and are highly suitable for applications requiring contact with pharmaceuticals, also after radiation sterilization. These compositions are also moldable by injection molding, and the resulting articles have excellent resealing capability and depending on the application very good tribological performance or resistance towards coring (fragment release in consequence of the puncturing with needle).

It has been also noticed that a pharmaceutical seal according to the invention shows an advantageously comparatively low moisture uptake, especially compared to thermoset rubber parts for the same purpose.

The radiation sterilized pharmaceutical seal preferably shows a compression set at 70° C. of 50% or less and the post-irradiation set of less than 40% at the dose of at least 15 kGy (kilogray).

The radiation sterilisable pharmaceutical seal preferably is a pharmaceutical stopper, a syringe gasket, a tip cap, a liner, or an o-ring. The invention is more specifically also concerned with the mentioned parts being sterilized.

The present invention also concerns a method of manufacturing said pharmaceutical seal, wherein said method comprises the steps of:

a) Pre-mixing at least one substance representing component B, with at least one substance representing component C and at least one substance representing component D b) compounding the obtained premix with component A and optionally a further portion of component B or D; and c) molding the resulting composition of step (b) into a pharmaceutical seal.

The above mentioned proposal of the process constitutes the best known mode of carrying out the invention, should however not be considered a limitation.

The present invention addresses also a method of radiation sterilization of a molded part, e.g. a pharmaceutical closure, the part being produced from components based on thermoplastic vulcanizates comprising isobutylene monomer units, which materials are, prior to irradiation, packed under an inert atmosphere in a container impermeable to oxygen, wherein the said packed materials are irradiated for sterilization. As to this, the invention provides for a method according to which prior to irradiation said parts are packed under an inert atmosphere in a container impermeable to oxygen, wherein the said packed closures materials are irradiated for sterilization, wherein further the radiation is selected from the group consisting of 20 gamma rays, X-rays and beta particles (e-beam) and a radiation dose is between 1-50 kGy.

More preferably the radiation doses are from 5-30 kGy. The closures are typically irradiated with a dose sufficient to reach a desired sterility assurance level.

DETAILED DESCRIPTION OF THE INVENTION

The present invention relates to a radiation sterilisable part, especially pharmaceutical seal or a sterilized part comprising:

(a) a composition obtained by blending an isobutylene-based, preferably pre-crosslinked polymer as component (A) with (b) at least one polyolefin or a non-crosslinked rubber or a TPV as component (B)

(c) at least one polymer having a Tg of 90° C. or higher as component (C) and (d)—preferably—at least one component (D) selected from the group of: substituted vinyl polymers, styrenic block copolymers, inorganic functionalized and non-functionalized fillers, carbon black, halogen scavengers, especially the inorganic halogen scavengers, acid acceptors and stabilizers, especially the polymeric stabilizers, and processing aids.

Component A

The component (A) of the present invention is a preferably crosslinked composition, more preferably cross-linked prior to blending ("pre-cross-linked") composition of the functionalized, isobutylene-based polymer described in detail in the US 2010/0249296 patent by Kaneka Corporation, which is incorporated herein by reference. As described there, the crosslinking of the isobutylene-based polymer is achieved in the presence of one or more cross-linking catalysts, a polyolefin and potentially other additives. Taking into account the representative examples defined in US 2010/0249296, the TPV material is produced specifically under reactive compounding conditions from the alkenyl end-functionalized isobutylene-containing polymer (either in form of a isobutylene homopolymer or a copolymer of isobutylene with other cationically polymerizable co-monomers, e.g. styrene and other aromatic vinyl compounds, dienes, etc.). Apart from the main isobutylene-based component, the representative TPV is said to contain—among others—also a polyolefin (although a high number of different polyolefins is available, mainly the random and isotactic versions of polypropylene are utilized due to advantageous cost-performance ratio), a softener (polybutene oil), a block copolymer and a lubricant (e.g. polyethylene wax). The crosslinking reaction is facilitated by the presence of special crosslinking agent-polysiloxane polymer functionalized with silyl groups (Si—H) and triggered by the cross-linking catalysts-particularly the organic complexes of platinum (most preferably with alkenyl-modified siloxane compounds). More specifically, the starting isobutylene-based polymer used for the production of a TPV, as mentioned in US 2010/0249296, should be characterized by the isobutylene monomer fraction of 50% by weight or more, preferably 70% by weight or more, or more preferably 90% by weight or more. Except for the capability of being polymerized under cationic conditions, no particular limitation is imposed on the potential co-monomers of isobutylene. Examples of the co-monomers proposed by the invention include aromatic vinyl derivatives, aliphatic olefins; dienes (such as isoprene, butadiene, and divinylbenzene; vinyl ethers or 3-pinene). The co-monomers may be used alone or in combination of two or more. Further, the topology of the isobutylene-containing copolymer is also not addressed, so a conceivable example such a copolymer maybe, e.g. an alkenyl-end-functionalized styrene-isobutylene-styrene block copolymer. Independently on the structure and composition, these isobutylene-based polymeric precursors (macromers) must bear unsaturated functionalities (preferably in terminal positions) capable of undergoing further cross-linking reactions—in particular of hydrosilylation type—to produce the final TPV. Therefore, such end-functionalized isobutylene-containing moiety combined with the listed additives and catalysts, must subsequently be subjected to a reactive compounding process in an appropriate mixer (e.g. a Banbury mixer, twin screw extruder or similar) at temperatures ranging from 130 to 240° C., finally yielding isobutylene-based thermoplastic vulcanizate (TPV).

With respect to the reported invention, the desired hardness of such TPV composition shall range from 15 to 85° ShA, more preferably between 25 and 75° ShA and even more preferably between 40 and 65° ShA to guarantee high efficiency of compounding and good interaction between components.

Component B

In the currently reported invention, the component (B) is at least one polyolefin resin or a non-crosslinked rubber or a TPV or a combination of them from following polymer groups:
a) homopolymers of ethylene, propylene, isobutylene, isoprene and 1-butene,
b) copolymers of ethylene, propylene, isobutylene, 1-butene, isoprene, α-olefins, cyclic olefins, conjugated or non-conjugated dienes other than isoprene, α-methylstyrene, para-methylstyrene, vinyl acetate, ethyl acrylate, maleic anhydride and products of their halogenation,
c) terpolymers of isobutylene, 1-butene, isoprene, α-olefins, cyclic olefins, conjugated or non-conjugated dienes, α-methylstyrene and para-methylstyrene, vinyl acetate, ethyl acrylate, maleic anhyrdride (other monomers to be added) and products of their halogenation.

The polyolefin resin is preferably characterized by sufficient melt viscosity to facilitate melt mixing/compounding that allows producing desired morphology of the compound. The melt flow index (MFI) has become widely accepted as helpful parameter allowing characterization and distinction of different, mainly linear, polymer types based on their flow behavior. The method is described in detail in the ASTM D1238 and ISO 1133 standards. Preferred polyolefin polymers used as the component B of the present invention show a melt flow index (MFI) in the range from 0.1 to 75 g/10 min at appropriate temperature (each polymer type has a recommended temperature for such measurement), preferably from 1 to 65 g/10 min, most preferably from 1 to 50 g/10 min. Polypropylene and polyethylene are the most typical examples of such materials, but their copolymers with other monomers (alfa-olefins, non-conjugated and conjugated dienes) can also be applied, with the provision on the flow behavior being substantially similar. Examples of such copolymers are ethylene-based resins such as polyethylene, an ethylene-propylene copolymer, an ethylene-propylene-non-conjugated diene copolymer, an ethylene-butene copolymer, an ethylene-hexene copolymer, an ethylene-octene copolymer, an ethylene-vinyl acetate copolymer, an ethylene-vinyl alcohol copolymer, an ethylene-ethyl acrylate copolymer, an ethylene-acrylic acid copolymer, an ethylene-methyl acrylate-maleic anhydride copolymer, and chlorinated polyethylene; propylene-based resins such as polypropylene, a propylene-ethylene random copolymer, a propylene-ethylene block copolymer, and chlorinated polypropylene; poly-1-butene; polyisobutylene; polymethylpentene and an ethylene-cyclic olefin copolymer (COC). The latter component shall preferably be characterized by the $T_g$ value in the range of 75-200° C., more preferably in the range of 110-180° C.

Among these, it is preferable, taking into account the chemical and functional properties of the compounds, to use polypropylene, copolymers of ethylene and dienes (cross-linkable PE, PE-X), copolymers of ethylene/propylene and dienes (EPDM) in form of a non-crosslinked rubber or a preformulated TPV material, homopolymers and copolymers of isobutylene, including the products of their chemical modification (halogenation), cyclic olefin copolymers, or a combination of them.

Examples of the polyethylene include linear low density PE, high density PE, copolymers of ethylene with dienes (PE-X), examples of polypropylene include random and isotactic homopolypropylene. Another example of the polyolefin is poly(1-butene), yet another example includes propylene-diene copolymers; ethylene/propylene/diene terpolymers and products of their reactive processing. Further examples include terpolymers of ethylene/propylene/norbornene and homopolymers or copolymers of isobutylene with isoprene or substituted vinyl polymers (e.g. para-methylstyrene) as well as products of their halogenation.

The utilization of polyolefins (component B) is generally preferred with respect to improved processability of the resulting compounds and good compatibility with the major elastomer component (butyl TPV—component A). However, the selection of components used to reach that effect should exhibit reduced tendency to leach out. That is normally achieved by introduction of the high molecular weight products—e.g. ethylene, propylene or isobutylene homopolymers showing the molecular weight of at least 3.0 kDa. In another aspect the utilization of the polyolefins (component B) is preferred due to increased stability of the resulting compounds towards ionizing radiation which is a consequence of termination/recombination reactions between free radicals and certain components (e.g. unsaturated (co)monomers) of the polyolefin phase. In further aspect, the introduction of polyolefins results in improved functional properties, e.g. coring properties in case of stopper closures or, for—another combination of polyolefins—in optimized tribological performance (e.g. lowered friction in case of syringe plungers).

The non-limiting examples of component B compositions are presented below.

In one of the embodiments of the current invention, the component (B) combines homopropylene with an ethylene/norbornene copolymer (cyclic olefin copolymer—COC), whereby both components are characterized by the MFI values (measured acc. to ISO 1133) in the range from 0.1 to 75 g/10 min, more preferably characterized by the MFI values of 15 to 65 g/10 min, most preferably characterized by the MFI values from 30 to 55 g/10 min, whereas the ethylene/norbornene copolymer COCs exhibit the Tg value ranging between 75 and 200° C., more preferably between 110 and 180° C.

In a further embodiment the component (B) combines homopropylene, high molecular weight polyisobutylene with ethylene/norbornene copolymers (cyclic olefin copolymer-COC), whereby the polypropylene is characterized by the MFI values (measured acc. to ISO 1133) in the range from 0.1 to 75 g/10 min, more preferably characterized by the MFI values of 15 to 65 g/10 min, most preferably characterized by the MFI values from 30 to 55 g/10 min and the COC copolymers are characterized by the MFI values in the range from 0.1 to 75 g/10 min, more preferably characterized by the MFI values of 1 to 65 g/10 min, most preferably characterized by the MFI values from 1 to 50 g/10 min.

In another embodiment, the component (B) combines homopropylene with an ethylene/norbornene copolymer (cyclic olefin copolymer—COC), whereby the polypropylene is characterized by the MFI values (measured acc. to ISO 1133) in the range from 1 to 75 g/10 min, more preferably characterized by the MFI values of 15 to 65 g/10 min, most preferably characterized by the MFI values from 30 to 40 g/10 min, and the ethylene/norbornene copolymer COCs is characterized by the MFI value of 0.1 to 75 g/10 min, more preferably between 1 and 25 g/10 min, most preferably between 10 and 15 g/10 min and exhibits the Tg value ranging between 75 and 200° C., more preferably between 110 and 180° C.

In a further embodiment, the component (B) combines homopropylene characterized by the MFI values (measured acc. to ISO 1133) in the range from 1 to 75 g/10 min, more preferably characterized by the MFI values of 15 to 65 g/10 min, most preferably characterized by the MFI values from 30 to 40 g/10 min, an ethylene/propylene-non-conjugated diene copolymer, either in form of a non-crosslinked rubber or a preformulated TPV, a high molecular weight polyisobutylene and with an ethylene/norbornene copolymer (cyclic olefin copolymer—COC) characterized by the MFI values of 0.1 to 75 g/10 min, more preferably from 10 to 60 g/10 min, most preferably from 10 to 20 g/10 min, said COC being characterized by the Tg value ranging between 75 and 200° C., more preferably between 110 and 180° C.

In yet a further embodiment, the component (B) combines homopropylene characterized by the MFI values (measured acc. to ISO 1133) in the range from 1 to 75 g/10 min, more preferably characterized by the MFI values of 15 to 65 g/10 min, most preferably characterized by the MFI values from 30 to 40 g/10 min, with an ethylene/propylene-non-conjugated diene copolymer, either in form of a non-crosslinked rubber or a preformulated TPV material and with ethylene/norbornene copolymers (cyclic olefin copolymers—COCs) characterized by the MFI values of 0.1 to 75 g/10 min, more preferably from 1 to 65 g/10 min, most preferably from 10 to 50 g/10 min and having a Tg value ranging between 75 and 200° C., more preferably between 110 and 180° C.

Component C

The component C of the present invention is preferably a polymeric material, characterized by high values of glass-transition and/or melting temperatures (higher than 90° C. as measured acc. to ISO 11357 or DIN53765) chosen from the group comprising polyimide, polyether-imide, polyamide-imides, polyetherketone, aliphatic and aromatic polyamides, aliphatic and aromatic polyesters, polyphenylene sulfide or polyphenylene ether (both in either pure form or in pre-mixes with other polymers—e.g. polystyrene).

With respect to the content of reported invention the polymers representing component C allow in one of the aspects to produce the compounds with optimized creep compliance after exposure to radiation (essential for pharmaceutical seals which need to stay, in case of assembled systems, under certain deformation in long term). A failure would lead to leaks or could result in deactivation of certain drugs in consequence of the contact with air.

In a composition according to the present invention, it is believed that the polymers representing component C exert a synergistic stabilizing effect towards free-radicals introduced by radiation sterilization and thus reduce the extent of degradation observable in case of main component A.

With respect to the content of the reported invention, all the materials used as component C are preferred to be pure grades, possibly free from or characterized by only limited fraction of the additives like stabilizers, antioxidants, antiozonants, mold-release agents, lubricants, flame retardants, dyes, pigments, etc. It is of essential importance, that such materials do not contribute to the increased levels of extractables and leachables or negatively influence chemical cleanliness of the final material. Practically, such materials shall be compliant with respect to their chemical cleanliness (particularly extractable moieties) with international pharmacopoeia standards (e.g. European or Japanese Pharmacopoeia). With respect to their purity, all the substances constituting the component C of the reported invention were found to be preferably characterized by the level of reducing substances (as measured acc. to the JP on untreated granules), lower than 1.5 ml of the $KMnO_4$ solution.

The polyimide, polyether-imide or polyamide-imide polymers used as component (C) are typically products of condensation processes between aromatic diamines and dianhydrides, but other monomers are also possible (e.g. J. E. Mark "Physical properties of polymers, handbook"). The materials, eventually in form of masterbatches or admixtures, exhibit Tg values (according to ISO 11357) ranging from 90 to 350° C., preferably between 120 and 300° C., more preferably between 130 and 280° C.

The polyaryletherketones applicable from the standpoint of the current invention exhibit Tg values (as measured acc. to the ISO 11357-2 or by another applicable method—e.g.

DMA/DMTA) ranging between 90 and 350° C., preferably between 120 and 300° C., more preferably between 150-280° C.

There are no special requirements regarding the utilization of eventual masterbatches/admixtures except for the only provision of their appropriate chemical cleanliness.

The aliphatic and aromatic polyamides used for the reported invention preferably represent the group comprising of e.g. polyamide/nylon 6, polyamide/nylon 66, nylon 11, nylon 12, nylon 6.10, nylon 6.12, copolymers of phenylene- and xylylene-diamines and their derivations with adipic acid or chloride, phtalic acids or their chlorides and their further derivatives. More preferably, the examples of polyamides interesting from the standpoint of the current invention include aromatic polyamides (aramides) in the type of the meta-nylon (nylon MXD) or para aramides. With respect to the processability, the utilized polyamides/polyaramides shall be characterized by the MFI values (acc. to ISO 1133) ranging from 0.01-90 g/10 min, more preferably from 0.1 to 45 g/10 min.

The representative examples of the polyester resins include polyethylene and polybutylene terephtalates, polyethylene isophtalate and their copolymers. Alternatively one may also consider utilization of the liquid crystalline polyesters. With respect to the processability, the utilized polyester resins shall be characterized by the MFI values (acc. to ISO 1133) ranging from 0.01-90 g/10 min, more preferably from 0.1 to 45 g/10 min.

Polyphenylene ether and polyphenylene sulfide (PPE and PPS, respectively) are preferably pure grades with possibly low level of extractables. The materials can be applied in pure form or eventually premixes with other polymers, e.g. PS when processability of the pure material becomes a technical concern. When the premixes of PPE with PS are concerned (or combinations of such premixes), they are preferably characterized by the Tg values, measured e.g. according the procedure described in the ISO 11357 standard, ranging from 90 to 280° C., more preferably from 120 to 250° C., most preferably from 135 to 220° C. Furthermore such premixes shall be characterized by typical MFI (ISO 1133) values ranging from 1-14 g/10 min, more preferably from 2-12 g/10 min, most preferably from 4 to 10 g/10 min.

Component D

Component D does not need to be part of the material at least concerning some applications.

If it is part of the material, it is preferred as component D, that it is a substance representing one of the following groups:
1. Substituted vinyl polymers such as aromatic vinyl compounds and more preferably polystyrene or syndiotactic polystyrene as aromatic vinyl compound.
2. Styrenic block copolymers
3. Functionalized and non-functionalized inorganic fillers:
4. Halogen scavengers
5. Carbon blacks
6. Acid acceptors
7. Special stabilizers
8. Processing aids The substituted vinyl polymers applicable with respect to the aim of the invention are mainly the aromatic vinyl compounds. The examples of such substances include the polymers of styrene, styrene derivatives substituted with aliphatic groups attached to both the aromatic ring or/and vinyl group as e.g. o-, m-, or p-methylstyrene, [alpha]-methylstyrene, [beta]-methylstyrene, 2,6-dimethylstyrene, 2,4-dimethylstyrene, [alpha]-methyl-o-methylstyrene, [alpha]-methyl-m-methylstyrene, [alpha]-methyl-p-methylstyrene, [beta]-methyl-o-methylstyrene, [beta]-methyl-m-methylstyrene, [beta]-methyl-p-methylstyrene, 2,4,6-trimethylstyrene, [alpha]-methyl-2,6-dimethylstyrene, [alpha]-methyl-2,4-dimethylstyrene, [beta]-methyl-2,6-dimethyl styrene, [beta]-methyl-2,4-dimethylstyrene, o-, m- or p-t-butyl styrene and similar. Further the examples of monomers include styrene derivatives of such kind substituted with halogen atoms. The example of other functionalized styrene monomers include o-, m-, or p-methoxy styrenes, styrene derivatives substituted by silyl groups, indene, and vinylnaphthalene. Among these, from a point of view of industrial availability and glass-transition temperature, atactic or syndiotactic polystyrene, poly([alpha]-methyl)styrene or poly(para-methyl)styrenes and mixtures of them are preferred. Typically, it is advantageous to use pure grades of the atactic and syndiotactic polystyrenes (denoted with PS and sPS, respectively), compliant in terms of extractable substances with international Pharmacopoeia standards, characterized by a molecular weight ranging from 50 to 500 kDa and MFI values from 1 to 65 g/10 min, more preferably from 10 to 20 g/10 min. More specifically, the untreated granulates of PS and sPS grades (as received from the supplier) utilized in reported invention were found to be compliant with the Japanese Pharmacopoeia standard regarding the level of reducing substances (consumption of the $KMnO_4$ solution lower than 1.5 ml). The introduction of certain small fraction of the styrenic polymers is preferred in terms of lowering the surface stickiness of the sterilized products, which observably improves machineability of the final products. Due to their ability to scavenge the free-radicals induced by the high-energy radiation, they also contribute together with the component C to the improved retention of good physical and chemical properties by the material after the radiation sterilization step.

The styrenic block copolymers constitute another group of additives. With respect to the aim of the current invention it is particularly preferred to use the styrenic thermoplastic elastomers. Examples of such copolymers include diblock and triblock copolymers of styrene representing the structure of AB or ABA as normally obtained in ionic polymerization processes. The commercially available embodiments of the ABA systems include the copolymers in which the polymers styrene or its derivatives constitute the external blocks. The other blocks are mainly composed of aliphatic olefins, dienes, silanes, vinylcarbazole, vinyl ethers, [beta]-pinene and acenaphthylene or the products of their modification by e.g. halogenation or hydrogenation. Such monomers can be used alone or in combination of two or more of them. More in detail, the examples of aliphatic olefin monomers include ethylene, propylene, isobutylene, 1-butene, 2-methyl-1-butene, 3-methyl-1-butene, pentene, hexene, cyclohexene, 4-methyl-1-pentene, vinylcyclohexane, octene and norbornene. The examples of diene monomers include butadiene, isoprene, hexadiene, cyclopentadiene, cyclohexadiene, divinylbenzene, and ethylidene norbornene. Furthermore, the examples of vinyl ether monomers include methyl vinyl ether, ethyl vinyl ether, (n-, iso)propyl vinyl ether, (n-, sec-, tert-, iso)butyl vinyl ether, methyl propenyl ether, and ethyl propenyl ether. Finally, the examples of a silane compound include vinyl trichlorosilane, vinyl methyldichlorosilane, vinyl dimethylchlorosilane, vinyl dimethylmethoxysilane, vinyl trimethylsilane, divinyldichlorosilane, divinyl dimethoxysilane, divinyldimethylsilane, 1,3-divinyl-1,1,3,3-tetramethyldisiloxane, trivinylmethylsilane, [gamma]-methacryloyloxypropyltrimethoxy-silane and [gamma]-methacryloyl oxypropylmethyl-dimethoxysilane.

In case of the styrenic block copolymers, both the fraction of styrene and the molecular weight of the constituent blocks shall be high enough to promote formation of the clearly defined domain microstructure. In most typical embodiments of the current invention the total molecular weight of the block copolymers ranges between 30 and 150 kDa, with the styrene content ranging from 15 to 65 wt. %. It is particularly advisable to use styrene-isobutylene-styrene copolymers (SIBS).

The functionalized and non-functionalized fillers of the current invention are represented by, but not limited to, materials such as so-called organomodified clays-usually functionalized with organosilane compounds, quaternary ammonium moieties or subjected to other treatment to facilitate their exfoliation, calcined and non-calcined clay types (preferably calcined ones), various talc versions (preferably high aspect ratio ones) and precipitated and fumed silicas. Talc and other fillers must be clean grades with respect to heavy metals content and Zn/Ca/Mg/Al extraction. An example of a suitable talc is HAR® talc manufactured by Luzenac. The fillers might be used separately or in form of admixtures.

The high purity furnace carbon black or channel carbon black or high purity conductive carbon black types exhibit sufficient cleanliness with respect to polynuclear hydrocarbons and other impurities. The carbon blacks used might be used separately or in admixtures.

The halogen and acid acceptors are represented by magnesium oxide, zinc oxide or admixtures of these filler types.

In one embodiment of the reported invention, the component D combines styrenic block copolymer (preferably having low gas permeability) with high aspect ratio talc. In another embodiment of the reported invention, the component D combines styrenic block copolymer (preferably having low gas permeability), high purity carbon black and high aspect ratio talc. In a further embodiment, the component D combines a styrenic block copolymer, polystyrene or syndiotactic polystyrene and high aspect ratio talc. In yet another embodiment the component D combines a styrenic block copolymer, polystyrene or syndiotactic polystyrene, high aspect ratio talc and high purity carbon black. In a further embodiment, the component D combines a styrenic block copolymer, high aspect ratio talc and a halogen scavenger.

Finally, with respect to the reported invention it is possible to introduce into the compound some stabilizers and processing aids, preferably characterized by sufficient compatibility with the matrix and high molecular weight that lead to reduced tendency to leach out, furthermore not affecting the chemical cleanliness or functional properties of the final material in a negative way. Examples of such stabilizers include, but are not limited to, substances like oligomeric and preferably polymeric products containing functional groups. More preferably, the stabilizers may represent the group of substances active towards the UV radiation, like e.g. compounds with functional units of hindered-amine light stabilizers (HALS). The processing aids are represented, but not limited to process oils of mineral or natural origin, as e.g. paraffinic, naphtenic or vegetable oils. However, as already mentioned their fraction should be limited due to the potential tendency to leach out and affect the performance of pharmaceutical formulation.

Without being bound to any theory, it is believed that component D is mainly added to fine-tune the physical and chemical properties of the final composition or to improve its processability. With respect to the modification of physical features, the modification aims e.g. at reduction of the creep compliance under load or the optimization of stress relaxation behavior. When the chemical characteristics of the final compounds are considered, some additives tend to impart additional stabilization helping to keep the free-radical reactions caused by irradiation under control.

Further it is noted that the chemical crosslinks present in the TPV materials (as the component A of the current invention), even when their density is relatively low as compared with thermoset rubbers, influence to a substantial extent the processability of compounds based on these TPV materials. Therefore, some of the aforementioned additives are believed to help optimize the rheological characteristics of the formulated compounds by improving the melt flow or the appearance of final products.

Method of Manufacturing a Part According to the Invention

The compounds of the reported invention are normally prepared by melt-mixing of the components in a suitable mixer. There are no special provisions related to the number of compounding operations unless an additional operation (pre-compounding) may be advantageous with respect to the state of dispersion achieved for particular additives.

Processing of chosen thermoplastic resins in a pre-compounding step yielding masterbatches applicable later. The pre-compounding is realized in a co-rotating twin-screw extruder (but other mixers are applicable as well).

The pre-compounding is realized preferably with temperature profile from 220-280° C. (entry and exit zones) and 220-340° C. (mixing zones), more preferably the temperatures range from 225 to 275° C. and from 250° C. to 300° C., respectively. In one aspect of the present invention it is advantageous to use screws providing high shear for efficient dispersive and distributive mixing.

Screw rotation must preferably stay in the range of 150-500 rpm (most preferably 200-400 rpm). The throughput of the extruder needs to guarantee the optimal mixing efficiency.

In the reported invention the pre-mix is formulated using at least one of the polymers representing component B with at least one of the polymers representing component C. With respect to the desired properties of the final compound, it is preferred to include in the premix at least one substance of component D, preferably one or more styrenic block copolymers and/or substituted vinyl polymers and/or modified or non-modified fillers and/or halogen scavengers and/or carbon black and/or acid acceptors and/or stabilizers and/or processing aids.

The aforementioned premix is then mixed with the main component A. This final compounding is carried out at the temperature profile ranging from 160 to 260° C., more preferably from 190 to 250° C., with an average screw speed ranging from 180-400 rpm, more preferably ranging between 200-320 rpm. If it is advantageous with respect to the compound properties, some further portions of component B or D can be introduced.

With respect to the next stage of processing which is molding of the produced compound into a desired shape (yielding pharmaceutical seals), the formulated material is preferably granulated and dried. There are no special limitations imposed on a method of granulation or the physical dimensions with the only exception that the form of material granules determines easy feeding of the molding equipment. Drying ensures appropriate humidity level to avoid problems with gas bubbles during molding.

With respect to the reported invention any of the molding methods can be chosen provided it assures reasonable productivity. It is preferable to mold the above mentioned compounds using an injection press. The injection molding is realized in a press equipped with an appropriate mold. Mold temperature facilitates achieving an optimal balance between the yield and material properties.

Sterilization

The molded closures may require sterilization prior to use. The sterilization utilizing radiation has recently gained on popularity due to several advantages. Particularly, for the TPE and TPV materials that are either uncured or characterized by only very low crosslink density, the radiation treatment means less risk of product deformation or displacement, when the elastomeric part is integrated into the total packaging system, e.g. a capped vial or a syringe.

The elastomeric materials products (closures, etc.) to be sterilized are preferably provided in any type of container/packaging material that is neither shielding off nor absorbing the utilized form of radiation. More precisely, this material/container shall neither interfere with the radiation and lower its energy, nor readily degrade under its influence. Furthermore, the said packaging material/container must be impermeable to gases, particularly to oxygen (reacting with free radicals to yield functional groups). Examples of such packaging materials include cerium-doped glass, blister films and pouches produced from certain thermoplastic resins, etc.

For the reported invention, the values of radiation dose are ranging between 1 and 50 kGy, more preferably from 5 to 30 kGy.

With respect to the gamma sterilization the closures of present invention can be manufactured from a compound comprising an isobutylene based TPV (thermoplastic vulcanizate), modified further by the addition of some selected substances, as already mentioned in preceding sections. The isobutylene-based TPV component represents preferably a type as obtainable from a composition comprising isobutylene-based, end-functionalized polymer (either polyisobutylene or a styrene-isoprene-styrene triblock copolymer) with terminal groups capable of undergoing hydrosillylation reaction in presence of a additional styrenic block copolymer, a polyolefin component, proper crosslinking catalyst and some several specific additives as defined in the US patent nr 2010/249296 by Kimura K., which is hereby incorporated by reference.

It is particularly advantageous to modify the aforementioned TPV material with at least one polyolefin such as olefin homopolymers and/or copolymers (e.g. homopolymers of ethylene, propylene, isobutylene, isoprene and 1-butene), furthermore statistical, alternating and block copolymers of those monomers, cyclic olefin copolymers, copolymers of ethylene and propylene with conjugated and non-conjugated dienes, copolymers of ethylene with α-olefins and substituted α-olefins, copolymers of ethylene and propylene with conjugated and non-conjugated dienes, and their mixtures.

The compounds of the present invention preferably further comprise at least one polymer exhibiting high $T_g$ value. Typically, such polymers are represented by polyimide, polyetherketone, aromatic and aliphatic polyamides, polyphenylene sulfide or polyphenylene ether. The polymer shows preferably a Tg of 90° C. or higher, more preferably a Tg between 120 and 300° C., most preferably a Tg between 135 and 280° C.

Furthermore, the compounds preferably comprise at least one component representing the group of substituted vinyl polymers in form of e.g. poly(2-vinylpyridine), poly(4-vinylpyridine), poly(N-vinylcarbazole), poly(4-vinylpyridine-co-styrene), atactic and syndiotactic polystyrene, poly (a-methylstyrene), poly(4-methylstyrene), poly(4-hydroxystyrene), poly(4-acetoxystyrene), poly(styrene sulfonic acid). Furthermore, the compounds comprise at least one additive selected from the groups of: styrenic block copolymers, preferably showing characteristics of a thermoplastic elastomer (TPE). Examples of such TPE materials include but are not limited to poly(styrene-butadiene-styrene) (SBS) and poly(styrene-isoprene-styrene) (SIS) block copolymer and products of their partial and complete hydrogenation e.g., poly(styrene-ethylene/propylene-styrene) block copolymer (SEPS), poly(styrene-isobutylene-styrene) (SIBS) block copolymer or similar.

It is furthermore advantageous with respect to the content of present invention, to modify the compound by addition of at least one substance representing the groups of: inorganic non-functionalized fillers, inorganic functionalized fillers such as e.g. organomodified clays functionalized with organosilane compounds, quaternary ammonium salts or subjected to other treatment to facilitate exfoliation, talc (preferably high aspect ratio HAR talc), clay (preferably calcined clay), precipitated and fumed silicas, high purity furnace carbon black or channel carbon black, each carbon black being characterized by sufficient cleanliness with respect to polynuclear hydrocarbons and other impurities, halogen scavengers, acid acceptors as represented by, but not only limited to, magnesium oxide and zinc oxide or admixtures of these filler types.

Finally, the compounds can optionally contain stabilizers (e.g. UV or gamma-stabilizers) that are characterized by high molecular weight and not affecting the chemical cleanliness. Examples include, but are not limited to, polymers with hindered aminic groups (HALS type stabilizers). Moreover, the compounds of the present invention can optionally contain processing aids which are represented, but not limited to process oils of mineral or natural origin, as e.g. paraffinic, naphtenic or vegetable oils. However, as already mentioned their fraction should be limited due to the potential tendency to leach out and affect the performance of pharmaceutical formulation.

All the components must preferably be characterized by a proper level of chemical cleanliness with respect to compliance with national and supranational standards (pharmacopoeia).

The compounds utilized in the reported invention shall be prepared by melt-mixing utilizing proper equipment, assuring sufficient temperature and shear levels to lower the viscosity of the compounds but still not resulting in excessive thermal and mechanical degradation of the material. Examples of such machines include, but are not limited to closed-chamber batch mixers (e.g. Brabender mixer, tangential mixer) and single and twin screw extruders. Preferably, a twin-screw extruder should be used as a mixer.

Furthermore the compounds used in the present invention shall be subsequently molded in the form of a pharmaceutical seal or closure (e.g. a stopper, gasket, tip cap, o-ring or a liner), or a self-sealing valve, an ear plug, an oxygen mask, a vibration damper, a catheter tip, a skin-contact patch, a pharmaceutical tubing, a pharmaceutical implant or the like using appropriate technique and tooling. The preferred molding methods include injection and compression molding.

As mentioned in preceding sections, the pharmaceutical seals (in form of stoppers, plungers, O-rings or similar shapes) must be encapsulated in a packaging material that is preferably neither shielding off nor absorbing the sterilizing radiation and does not readily degrade under its influence. The latter feature is essential to avoid contamination of the encapsulated products with degradation products or other substances that may leak from the packaging material.

The packaging material must also be characterized by barrier properties sufficient to reduce the exposure of the encapsulated products to air or more preferably to oxygen. As generally accepted, free radicals present on the surface and in the bulk of irradiated material tend to undergo consequent reactions with oxygen that lead to formation of active terminal and pendant functional groups (examples include, but are not limited to, carboxyl and hyrdoxyl groups). Presence of such moieties affects significantly the level of chemical cleanliness of the said products and may lead to failure.

The examples of appropriate packaging materials include, but are not limited to cerium-doped glass, blisters films, pouches or bags produced from thermoplastic resins or laminate foils with aluminum interlayers. Preferably, the packaging materials used comprise foil bags, most preferably, the packaging materials comprise foil bags with multilayer structure (in which one or more layers are characterized by very good gas-barrier performance).

The encapsulation shall take place in a device that allows working with the products under a well-defined, inert atmosphere. The inert atmosphere is considered—an atmosphere containing only a minor fraction or even is devoid of oxygen, preferably an atmosphere comprising nitrogen and/or argon, more preferably an atmosphere comprising at least 90 vol. % of nitrogen or argon, more preferably said atmosphere comprising 95 vol % of nitrogen or argon and about 5% vol. of other gases (e.g. hydrocarbons, oxygen, etc.), most preferably the atmosphere comprising at least 99 vol. % of nitrogen or argon and less than 1% of impurities (including hydrocarbons, oxygen and other gases). The products to be encapsulated shall not be exposed to air or oxygen during the whole encapsulation process.

Ranges, Values

The ranges, e.g. value ranges or multiple ranges, mentioned before and hereafter, do enclose for the purpose of disclosure also any intermediate value. Especially they do enclose such intermediate value by 1/10 steps of the respective dimension, in the given case also dimensionless. This means e.g. 1/10 of a length, of a hardness, e.g. ShA, of a melt flow index (MFI); g/10 min), of a molecular weight (kDa), of a mm, of a degree, of a %, especially wt. % etc., or even of an x-multiple. The next value is then e.g. in case of explicitly mentioned (starting-) value 1 mm: 1.1 mm or 0.9 mm, in case of a closing value of a disclosed range, or in case of an explicitly mentioned value 50 wt %: 50.1 wt % (or 49.9 wt %) etc. This applies to both, the restriction of a range from top and/or bottom as well as the disclosure of one or more singular values within a disclosed range.

As far as the description refers to specific terms in brackets such as (inorganic) halogen scavengers or (polymeric) stabilizers or beta (electron beam), the disclosure is always that the term behind the term in brackets or the term before the term in brackets in the latter case may stand alone but preferably it can be the specific term including the term in brackets. With reference to the said examples, the component D can be selected among others from halogen scavengers and preferably from inorganic halogen scavengers or from stabilizers and preferably from polymeric stabilizers. Further, the method of radiation sterilization can be an electron beam irradiation, specifically a beam irradiation.

Examples

The reported invention can be further explained by following examples.

The compounded materials were evaluated with respect to their physical, functional and chemical properties. The protocol for physical tests consisted of following analyses:

Test 1: hardness measurement following the ISO 7619-1.

A standardized specimen is taken for the tests, the hardness is to be measured at 3 to 5 different points on the surface with appropriate durometer (compliant with Shore A scale).

The results are recorded and the average value is calculated afterwards. The hardness value is recorded after a defined time of contact between the indenter and material surface, usually 15 s.

Test 2: compression set measurement following the specifications derived from the ISO 815 standard.

The test exists in 3 versions, differing by the temperature and time conditions:

2A. Compression set at 70° C., 24 h
2B. Compression set at 121° C., 0.5 h
2C. Post-irradiation (25 kGy) compression set at room temperature In all the cases a cylindrical test piece (cylinder diameter of 13±0.5 mm, height of 6.3±0.3 mm) is compressed to 75% of its original height in a special jig and exposed afterwards to the predefined conditions (following the cases 2A/B/C).

After the evaluation is finished, the test pieces are removed from the jigs and their height is measured again after 30 min. (2A+2B) or 24 h (2C) of relaxation. The compression set is calculated based on the initial and final height values—the lower the permanent deformation, the better the performance of the particular compound.

Test 3: relative viscosity of the compounds

Viscosity evaluation was based on the capillary rheometry data recorded for the investigated materials. The data presented in the chart show the relative compound viscosity, calculated with respect to the appropriate reference material: RM1 for compounds C1 and C2, and RM2 for compounds C3-C8. In all the cases a reduction of viscosity was observed for the compounds over a broad range of shear rates ($10^2$-$10^4$ $s^{-1}$), with the extent of reduction differing a bit for each particular shear rate value.

The protocol for functional tests consisted of:

Test 4: determination of the fragmentation

Fragmentation is defined by the number of material pieces released in consequence of piercing the closure with a needle.

For the sake of current tests, the procedure defined in EP/USP has been implemented. The results (number of fragments found) shall be lower than 5 pcs per 48 piercings.

Test 5: resealing

Resealing defines the ability of an elastomeric product to maintain tightness after being punctured with a needle. Currently reported tests were organized according to the procedure defined in EP/USP.

The main criterion is a number of closures that show no leak after being pierced with a needle. In general, 10 closures are tested and none of them may show a leak.

Test 6: stickiness after gamma exposure

Stickiness was defined by an indirect method—a certain amount of closures was allowed to stay in direct surface contact. After the predefined time, the tendency to form aggregates was evaluated with a subjective scale ranging between 1 (means no aggregates) and 5 (means predominant aggregate formation). The more stable the aggregates (e.g. against mechanical action), the higher the score.

Test 7: gliding behavior of the plunger

The forces related to the activation and gliding of a plunger in a syringe barrel are measured upon using the regular tensile machine in compression mode. A plunger is forced to move with a constant speed (v=100 mm/min) over a defined distance, whereas the values of the force necessary to start and maintain the movement are measured. The plungers are then compared with each other.

The results measured for TPV plungers were compared with the values obtained for the thermoset rubber (TSR)-based closures.

Test 8: seal integrity test for plungers

The plungers are tested using regular syringe barrels for the sealing performance. The assembled plunger is pushed with certain pressure and the eventual leaks of the coloured test liquid over the rills of the plunger are detected. In general none of the tested plungers should show a leak.

The investigated compounds, injection molded in form of a pharmaceutical closures (stoppers) or regular test pieces, were also thoroughly studied to evaluate their chemical cleanliness. The basic test criteria and procedures are specified in the European Pharmacopoeia (chapters about cleanliness standards defining water for injection (WFI)) and the Japanese Pharmacopoeia (chapters about extractable substances in rubber materials). For the sake of the reported investigation, the WFI test protocol based on the EP is denoted as chemical Test Protocol 1, whereas the test protocol based on the JP is further called Test Protocol 2. In either case, cleanliness analyses refer to the examination of aqueous extracts produced by extraction of the rubber material at 121° C. The test program included, among others, investigation of the:

a) pH change compared to a blank reference,
b) level of reducing substances—in a reaction with potassium permanganeate,
c) UV spectrum,
d) transmission of light,
e) foam test,
f) magnesium, calcium and zinc content,
g) residue after evaporation
h) acidity-alkalinity levels, Both types of sterilization procedures—steam treatment and gamma irradiation—were applied. The samples of steam- or gamma-treated materials are classified based on compliance with the chemical test protocols 1 and 2 mentioned above. The average irradiation dose applied to the samples differs with respect to the test protocol—for test protocol 1 (TP1) it is at least 15 kGy, whereas for the test protocol 2 (TP2) it is at least 25 kGy. The closures for the gamma-sterilization tests were sealed in special barrier bags under inert/protective atmosphere and then sent for irradiation. The sterilization was carried out at the target doses of 15 and 25 kGy—the real values of absorbed doses were determined with appropriate dosimeters.

The irradiated closures were stored under inert atmosphere conform with the purity requirements specified in the preceding section in sealed bags until start of the tests. The samples were then unpacked just prior to testing to avoid subsequent reactions with oxygen. The non-irradiated materials provided the reference.

The following examples are described:
a) Compounds 1 and 2 (C1 and C2) based on butyl TPV 1,
b) Compounds 3-8 (C3 to C5) based on butyl TPV 2, The non-modified butyl TPVs 1 and 2 constituted the reference materials and are further labelled as RM1 and RM2. The above mentioned butyl TPV's were not particularly modified against gamma-caused degradation. Based on our observations we classified the TPV-2 as being more stable with this respect. Both reference materials are characterized by high purity, but are very demanding in processing as consequence of their melt viscosity and elasticity and do not provide optimal functional performance.

| | Sample | | | | | | | | | |
|---|---|---|---|---|---|---|---|---|---|---|
| | RM1 | C1 | C2 | RM2 | C3 | C4 | C5 | C6 | C7 | C8 |
| Type of the Butyl TPV | 1 | 1 | 1 | 2 | 2 | 2 | 2 | 2 | 2 | 2 |
| Test 1 [°ShA] | 35.0 | 39.3 | 40.0 | 45.0 | 51.8 | 47.8 | 47.0 | 45.5 | 43.3 | 45.0 |
| Test 2A [%] | 24.2 | 24.5 | 25.3 | 28.0 | 29.0 | 28.0 | 30.7 | 27.1 | 27.5 | 29 |
| Test 2B [%] | 73.7 | 71.1 | 70.7 | 67.0 | 68.6 | 68.7 | 70.1 | 66.7 | 68.0 | 70.0 |
| Test 2C [%] | 20.1 | 18.7 | 18.2 | 24.0 | 22.5 | 21.5 | 22.0 | 23.0 | 23.5 | 23.0 |
| Test 3 [%] | 100 | 52-83 | 52-84 | 100 | 75-92 | 78-88 | 75-90 | 65-84 | 58-82 | 60-80 |
| Test 4 [—] | 0 | 1 | 2 | 4 | NT | 0 | 3 | NT | NT | NT |
| Test 5 [—] | 0 | 0 | 0 | 0 | NT | 0 | 0 | NT | NT | NT |
| Test 6 [—] | 5 | 3 | 3 | 4 | 1 | 2 | 2 | 1 | 1 | 1 |
| Test 7-activation force | NT | NT | NT | 3-5 | 3-5 | 3-5 | 3-5 | 3-4 | 3-4 | 3-4 |
| Test 7-gliding force [N] | NT | NT | NT | <3 | <2.5 | <2.5 | <2.5 | <2.5 | <2.5 | <2.5 |
| Test 8 [—] | NT | NT | NT | NT | 0 | 1 | 1 | 0 | 0 | 0 |
| Test protocol 1-WFI (min. dose 15 kGy) [—] | Not passed | Passed | Passed | Passed | Passed | Passed | Passed | Passed | Passed | Passed |
| Test protocol 2-JP (min. dose 25 kGy) [—] | Passed | Passed | Passed | Passed | Passed | Passed | Passed | Passed | Passed | Passed |

NT (not tested) is used when the specific parameter was considered not essential with respect to the final application of the particular compound and has not been investigated or when the test turned out impossible (e.g. due to deformation of the sample in consequence of heat treatment)

Preferred compositions of the pharmaceutical seal are provided in-below table:

| Component | Preferable concentration range [wt. %] | More preferred concentration range [wt %] | Most preferred concentration range [wt. %] |
|---|---|---|---|
| butyl TPV (Component A) | 50-99 | 60-98 | 70-90 |
| polyolefin or combination of polyolefines (component B) | 0.01-50 | 0.1-30 | 6-14 |
| high $T_g$ polymer or their combination (component C) | 0.01-50 | 0.1-30 | 1-6 |
| Component D | 0.01-50 | 0.1-35 | 0.3-20 |

Improvement in crucial chemical properties observed for the selected compounds irradiated under protective atmosphere (reference point: values for samples irradiated under normal atmosphere)

| Compound Type of the butyl TPV | Test protocol | real dose [kGv] | C1 1 | C2 1 | C3 2 | C4 2 |
|---|---|---|---|---|---|---|
| pH shift | 1 | 19.0-23.2 | −35% | −22% | −12.7% | −52.2% |
| RS | | | −17.6% | −11.5% | −15.3% | −18.4% |
| UV | | | −16.6% | −10.0% | −14.5% | −12.8% |
| pH shift | 2 | 31.0-32.5 | −12.5% | −37.4% | −41.1% | −14.10% |
| RS | | | −20.8% | −12.8% | −25.5% | −16.2% |
| UV | | | −22.0% | −12.5% | −15.1% | −8.3% |

In contrast to the reference materials, the compounds of the present invention are characterized by the desirable combination of physicochemical and functional properties. The introduction of additional components (B, C, D) helps in improving their functional features and overall processability, yet not affecting their physical and chemical characteristics negatively.

The compounds were found compliant with the stringent chemical requirements. Upon using the appropriate combination of packaging materials and protective atmosphere they can also be gamma sterilized without substantial deterioration.

The invention claimed is:

1. An elastomeric component having pharmacological compatibility, established by pharmacopeia standards, comprising a material comprising a composition obtained by blending:
   (a) a pre-crosslinked isobutylene-based thermoplastic vulcanizate material having hardness values ranging between 15-85 ShA as component (A);
   (b) at least one polyolefin or a non-crosslinked rubber or a thermoplastic vulcanizate as component (B);
   (c) at least one polymer having a glass transition temperature of 90° C. or higher as component (C); and
   (d) at least one component (D) selected from the group of: substituted vinyl polymers, styrenic block copolymers, inorganic functionalized and non-functionalized fillers, carbon black, halogen scavengers, acid acceptors, stabilizers and processing aids,
   wherein the component (A) has a concentration range of 50-85 weight percent of the elastomeric component;
   wherein the component (A) has an isobutylene monomer fraction of 70 percent by weight or more;
   wherein the pre-cross-linked isobutylene-based thermoplastic vulcanizate material bears unsaturated functionalities; and
   wherein the elastomeric component contains no low molecular weight processing oil.

2. An elastomeric component having pharmacological compatibility, established by pharmacopeia standards, comprising a material comprising a composition obtained by blending:
   (a) a pre-crosslinked isobutylene-based thermoplastic vulcanizate material having hardness values ranging between 15-85 ShA as component (A);
   (b) at least one polyolefin or a non-crosslinked rubber or a thermoplastic vulcanizate as component (B);
   (c) at least one polymer having a glass transition temperature of 90° C. or higher as component (C); and
   (d) at least one component (D) selected from the group of: substituted vinyl polymers, styrenic block copolymers, inorganic functionalized and non-functionalized fillers, carbon black, halogen scavengers, acid acceptors, stabilizers and processing aids,
   wherein the component (A) has a concentration range of 50-85 weight percent of the elastomeric component;
   wherein the component (A) has an isobutylene monomer fraction of 80-85 percent by weight;
   wherein the pre-cross-linked isobutylene-based thermoplastic vulcanizate material bears unsaturated functionalities; and
   wherein the elastomeric component contains no low molecular weight processing oil.

3. The elastomeric component according to claim 2, wherein the component (A) has hardness values ranging between 25 and 75 ShA.

4. The elastomeric component according to claim 2, wherein the component (B) is chosen out of polypropylene, high molecular weight polyisobutylene, cyclic olefin copolymer, co- or terpolymer of ethylene, propylene and diene, untreated or halogenated co- or terpolymers of isobutylene, isoprene and paramethylstyrene, or a combination of them, in either non-crosslinked or crosslinked form.

5. The elastomeric component according to claim 2, wherein the component (B) comprises an ethylene-cyclic olefin copolymer (COC) having a melt flow index (MFI) value ranging between 1 and 75 g/min and having a glass transition temperature value ranging between 75 and 200° C.

6. The elastomeric component according to claim 2, wherein the component (C) is selected from the group comprising: polyimide, polyether-imide, polyamide-imides, polyetherketone, aliphatic and aromatic polyamides, aliphatic and aromatic polyesters, polyphenylene sulfide or polyphenylene ether.

7. The elastomeric component according to claim 2, comprising polystyrene wherein the elastomeric component is showing a compression set after 24 hours at 70° C., of 50% or less and a post-irradiation set of less than 40% at the dose of at least 15 kGy.

8. The elastomeric component according to claim 2, wherein said elastomeric component is or is part of a self-sealing valve, an ear plug, an oxygen mask, a vibration damper, a catheter-tip, a skin-contact patch, a pharmaceutical tubing, an implant device or a seal.

9. A method of manufacturing a part according to claim 2, wherein said method comprises the steps of:
   a) pre-mixing at least one substance representing component (B), with at least one substance representing component (C) and at least one substance representing component (D)
   b) compounding the obtained premix with component (A) and optionally a further portion of component (B) or (D); and
   c) molding the resulting composition of step b) into a pharmaceutical seal.

10. The method according to claim 9, further comprises a step of sterilizing the molded pharmaceutical seal by means of radiation, preferably gamma-radiation, beta particles or X-ray.

11. The method according to claim 10, wherein, preferably, the molded pharmaceutical seal is irradiated with a total dose ranging between 1-50 kGy, more preferably 5-30 kGy.

* * * * *